(12) United States Patent
Gidekel et al.

(10) Patent No.: US 7,485,445 B2
(45) Date of Patent: Feb. 3, 2009

(54) PLANT GENE AND USES THEREOF

(75) Inventors: Manuel Gidekel, Temuco (CL); Ana Gutierrez, Temuco (CL); Claudia Rabert, Temuco (CL); Gustavo Gabrera, Temuco (CL); Jaime Sanchez, Temuco (CL); Leon Bravo, Comuna de Coronel (CL)

(73) Assignee: Vitrogen S.A., Las Condes, Santiago (CL)

( * ) Notice: Subject to any disclaimer, the term of this patent is extended or adjusted under 35 U.S.C. 154(b) by 0 days.

(21) Appl. No.: 11/787,383

(22) Filed: Apr. 16, 2007

(65) Prior Publication Data

US 2008/0253977 A1    Oct. 16, 2008

(51) Int. Cl.
*C12N 9/20* (2006.01)
*C12N 1/20* (2006.01)
*C12N 15/00* (2006.01)
*C07H 21/04* (2006.01)

(52) U.S. Cl. .................. 435/198; 435/252.3; 435/320.1; 536/23.2

(58) Field of Classification Search ................. 435/198, 435/252.3, 320.1; 536/23.2
See application file for complete search history.

(56) References Cited

OTHER PUBLICATIONS

Accession No. CD925971 (Jul. 15, 2003).*

* cited by examiner

*Primary Examiner*—Tekchand Saidha
(74) *Attorney, Agent, or Firm*—Dodds and Associates; John Dodds; L. Susanne Somersalo (57) ABSTRACT

A novel gene isolated from *Deschampsia antarctica* coding for a lipase like protein is disclosed. A system for production of recombinant enzyme is also disclosed as well as uses for the enzyme.

9 Claims, 9 Drawing Sheets

```
> gi|51038104|gb|AAT93907.1| putative GDSL lipase/acylhydrolase [Oryza sativa (japonica cultivar-group)]
  gi|55168051|gb|AAV43919.1| putative GDSL lipase/acylhydrolase [Oryza sativa (japonica cultivar-group)]
Length=101

Score = 84.7 bits (208), Expect = 1e-15
Identities = 56/101 (55%), Positives = 70/101 (69%), Gaps = 4/101 (3%)
Frame = +1

Query  1    MFAIKYGPVANHTKYGIENPLMVCCgnggppynfnpgkfgCG----DLCGPEARVLSWDGV  171
            MFAIKY  VANHTK +GIE PLM  CCG+GGPPYN++P K       DLC     +SWDGV
Sbjct  1    MFAIKYDLVANHTKHGIEKPLMTCCGHGGPPYNYDPKKSCTANDKDLCKLGEKFISWDGV   60

Query  172  HFTDFGSGLAAKHVMSGEYSKPRVKL-ASLINGGSKKSSSL  291
            HFTD  + A   V+SGE+S  PR+KL AS++    K+S L
Sbjct  61   HFTDAANEIVASKVISGEFSIPRIKLTASVVRPKKAKMSRL  101
```

Fig. 1

```
                                                                                      Section 1
           (1) 1          10         20         30         40         50         60
      Da   (1) MFAIKYGFVANHTKYGIEWPLMVCCGNGGPPYNENPGK---FGCGDLCGPEARVLSWDGVHFTDFGSGWAAKH
      Os   (1) MFAIKYDLVANHTKHGIEKPLMTCCGHGGPPYNYDPKKSCTANDKDLCKLGEKFLSWDGVHFTDARNELVASK
Consensus    (1) MFAIKY  VANHTKHGIE PLM CCG GGPPYNF P K      DLC   K ISWDGVHFTD A   I A  \
                                                                                      Section 2
          (77) 77         90        101
      Da  (74) GEYSKPRVKLASLINGGSKKSSSL-
      Os  (77) GEFSIPRIKLTASVVRPKKAKNSRL
Consensus   (77) GEFS PRIKL A I    K  S
```

```
                                                                              Section 1
         (1)  1         10        20        30        40        50        60
Da       (1)  ------------------------------------------------------------
Os       (1)  ------------------------------------------------------------
At       (1)  ---------GDSNSDTGGLVAGLGYPIGFPNGRLFFRRSTGRLSDGRLLIDFLCQSLNTSLLRPYLDSLGRT
CaA      (1)  MRVSLRSITSLLAATAAVLAAPAAETLDRRAALPNPYDDPFYTTPSNLGTFAKGQVIQSRKVPTDLGNANNA
CaB      (1)  --------MKLLSLTGVAGVLATCVAATPLVKRLPSGSDPAFSQPKSVLDAGLTCQGASPSSVSKPLLLVPGT
Consensus (1)             S    A L A                             L      Q      V  I
                                                                              Section 2
         (77) 77        90        100       110       120       130       140
Da       (1)  ------------------------------------------------------------
Os       (1)  ------------------------------------------------------------
At      (67)  NVANFAIAGSSTLPKNVPFSLNIQVKQFSH--FKSRSLELASSSNSLKGMFISNNGFKNALYMIDIGQNDLAI
CaA     (77)  QLQYRTTNTQNEAVADVATVWIPAKPASPPKIFSYQVYEDATALDCAPSYSYLTGLDQPNKVTAVLDTPILIG
CaB     (69)  GPQ---SFDSNWIPLSTQLGYTPCWISPPP--FMLNDTQVNTEYMVNAITALYAGSGNNKLPVLTWSQGGLVA
Consensus(77)                                 F        T                                I
                                                                              Section 3
        (153) 153       160       170       180       190       200       210
Da       (1)  ------------------------------------------------------------
Os       (1)  ------------------------------------------------------------
At     (141)  RGNSYSQTVKLIPQIITEIKSSIKRLYDEEGRRFWIHNTGPLGCLPQKLSMVKSKDLDQLGCLVSYNSAATLF
CaA    (153)  QQGYYVVSSDHEGFKAAFIAGYEEGMAILDGIRALKNYQNLPSDSKVALEGYSGGAHATVWATSLAESYAPEI
CaB    (140)  LTFFPSIRSKVDRLMAFAPDYKGTVLAGPLDALAVSAPSVWQQTTGSALTTALRNAGGLTQIVPTTNLYSATI
Consensus(153)                         L                    L                      A
                                                                              Section 4
        (229) 229       240       250       260       270       280       290
Da       (1)  ------------------------MFAIKYGFVANHTKYGIEWPLMVCCG-------NGG--------PP
Os       (1)  ------------------------MFAIKYDLVANHTKHGIEKPLMTCCG-------HGG--------PP
At     (217)  LDHMCEELRTELRDATIIY------IDIYAIKYSLLANSNQVGFKSPLMACCG-------YGG--------TP
CaA    (229)  GASHGGIPVSAKDTFTFLNGGPFAGFAIAGVSGLSLAHPDMESFIEARLNAKGQRTLKQIRGRGFCLPQVVLT
CaB    (216)  QPQVSNSPLDSSYLFNGKN------VQAQAVCGPLFVIDHAGSLTSQFSYVVG-------RSL--------LR
Consensus(229)                         MFAIKY LVAN  YGI  PLM CCG       GG         P
```

FIG. 4. (1 of 2)

```
                                                                                            Section 5
          (305)  305      310       320       330       340       350       360       370
    Da    (35)  NPGK---FGCGDLCGPEARVLSWDGVHFTDFGSGLAAKHVMSG--EYSKPRVKIASLINGGSKKSSSL-----
    Os    (35)  DPKKSCTANDKDLCKLGEKFISWDGVHFTDAANEIVASKVISG--EFSIPRIKITASVVRPKKAKNSRL----
    At   (272)  NVKIICGHKGSNVCKEGSRFISWDGIHVTG------------------------------------------
    CaA  (305)  LNVFSLVNDTNLLNEAPIASILKQETVVQAEASYTVSVPKFPRFIWHAIPDEIVPYQPAATYVLEQCAKGANI
    CaB  (271)  GQARSADYGITDCNPLPANDITPEQKVAAAALLAPAAAALVAGPKQNCEPDIMPYARPFAVGKRTCSGIVTP-
Consensus (305)      KS       DLC   AR ISWDGVHFTA A    A  VISG    S PILA     A K   S
                                                                                            Section 6
          (381)  381      390       400       410       420       430       440
    Da    (98)  ------------------------------------------------------------------------
    Os   (102)  ------------------------------------------------------------------------
    At   (302)  ------------------------------------------------------------------------
    CaA  (381)  PYPIAEHLTAEIFGLVPSLWFIKQAFDGTTPKVICGTPIPAIAGITTPSADQVLGSDLANQLRSLDGLQSAFGH
    CaB  (343)  ------------------------------------------------------------------------
Consensus (381)
                                                                                            Section 7
          (457)  457  462
    Da    (98)  ------
    Os   (102)  ------
    At   (302)  ------
    CaA  (457)  GPITPP
    CaB  (343)  ------
Consensus (457)
```

1,2-o-Dilauryl-rac-glycero-3-glutaric acid (6-methylresorufin)ester

Lipase/Colipase 1,2-o-Dilauryl-rac-glycerin + Glutaric acid (6-methylresorufin)-ester spontaneous degradation Glutaric acid (6-methylresorufin)-ester ⟷ Glutaric acid + Methylresorufin

PLANT GENE AND USES THEREOF

BACKGROUND OF THE INVENTION

1. Field of the Invention

The present invention relates generally to the field of plant molecular biology. More specifically the invention relates to nucleic acid fragment encoding plant lipase and uses thereof.

2. Description of Related Art

Lipases (triacylglycerol acylhydrolase, EC 3.1.1.3) belong to the family of hydrolases that act on carboxylic ester bonds. In addition to their natural function of hydrolyzing carboxylic ester bonds, lipases can catalyze esterification, interesterification, and transesterification reactions in non aqueous media. Due to this versatility lipases have a variety of potential applications for industrial uses. Examples of fields where lipases have applications are such as dairy industry, detergents, oleo chemical industry, pharmaceutical and cosmetic industry, medical and environmental applications. Depending on the process, the required characteristics of the lipase enzymes are different. For purposes where for example processing temperatures are high, one would need to have enzyme with high optimal temperature, for another process one may need to have an enzyme having low pH tolerance etc. Moreover, the modern biotechnology has enabled production of industrial enzymes such as lipases cell cultures, whereby the production costs can be dramatically lowered.

GDSL lipases are an important family of lipases. GDSL lipases are widely found in microbes, and a number of bacterial GDSL genes have been cloned and characterized. GDSL lipases are also found in plant species, and several candidates from various plant species such as *Arabidopsis thaliana, Rauvolfia serpentina, Medigago sativa, Hevea brasiliensis, Brassica napus, Oryza sativa* and *Alopecurus myosuroides* have been isolated, cloned and characterized.

Due to the large variety of industrial uses where lipase enzymes can be used, there is a clear need to identify and characterize new enzymes and genes coding for them and provide systems for industrial production of the enzymes.

Accordingly, identification and characterization of genes coding for lipase like proteins in plant species tolerant to low temperatures can provide novel enzymes for industrial applications. A plant species extremely tolerant to low temperatures is *Deschampsia antarctica* Desv. (Poacea). Accordingly, we have studied the gene expression of this vascular plant naturally colonizing Maritime Antarctic Peninsula.

SUMMARY OF THE INVENTION

Due to the increased interest in lipases in various fields of industry, there is a clear need for novel lipase enzymes. Especially, there is a need for novel lipase enzymes functional in wide range of temperatures. Moreover, there is a need for a method for economic production of lipase enzymes.

Accordingly, an object of the current invention is to provide a novel recombinant lipase, which is psycrophilic and can therefore stand low temperatures.

Another object of the current invention is to provide a simple and rapid method of producing lipase enzyme in host cell and subsequent purification of recombinant lipase.

An even further object of the current invention is to provide a novel lipase that can be used in waste water cleaning.

A further object of the current invention is to provide a novel lipase to be used as a component in sun screens.

According to a preferred embodiment the lipase enzyme is encoded by a nucleotide sequence essentially according to SEQ ID NO: 1 isolated from *Deschampsia antarctica*.

In a preferred embodiment, lipase enzyme of the present invention comprises the amino acid sequence essentially according to SEQ ID NO: 2.

Yet another embodiment of the present invention is a chimeric gene comprising an isolated nucleotide sequence encoding lipase like protein of *Deschampsia antarctica*.

An even further embodiment of the present invention is isolated host cells comprising the chimeric gene. The host cell may be eukaryotic, such as yeast or a plant cell, or it may be prokaryotic such as a bacterial cell. According to one embodiment the host cell comprising the chimeric gene is a *Pichia* cell.

An even further embodiment of the instant invention is to provide a process for cultivating host cells comprising the chimeric gene and isolating the recombinant enzyme produced in the cells.

Yet another embodiment of the instant invention is to provide a lipase enzyme for purposes of waste water cleaning.

An even further embodiment of the instant invention is to provide a sunscreen comprising the plant lipase of this invention.

DETAILED DESCRIPTION OF THE INVENTION

A cDNA expression library was obtained by using DNA samples of *Deschampsia antarctica*. This library enabled identification of one gene which encoded a lipase-like enzyme (triglyceride lipases EC 3.1.1.3). The cDNA gene sequence encoding the lipase of *Deschampsia antarctica* is according to SEQ ID NO:1.

Figure 1:
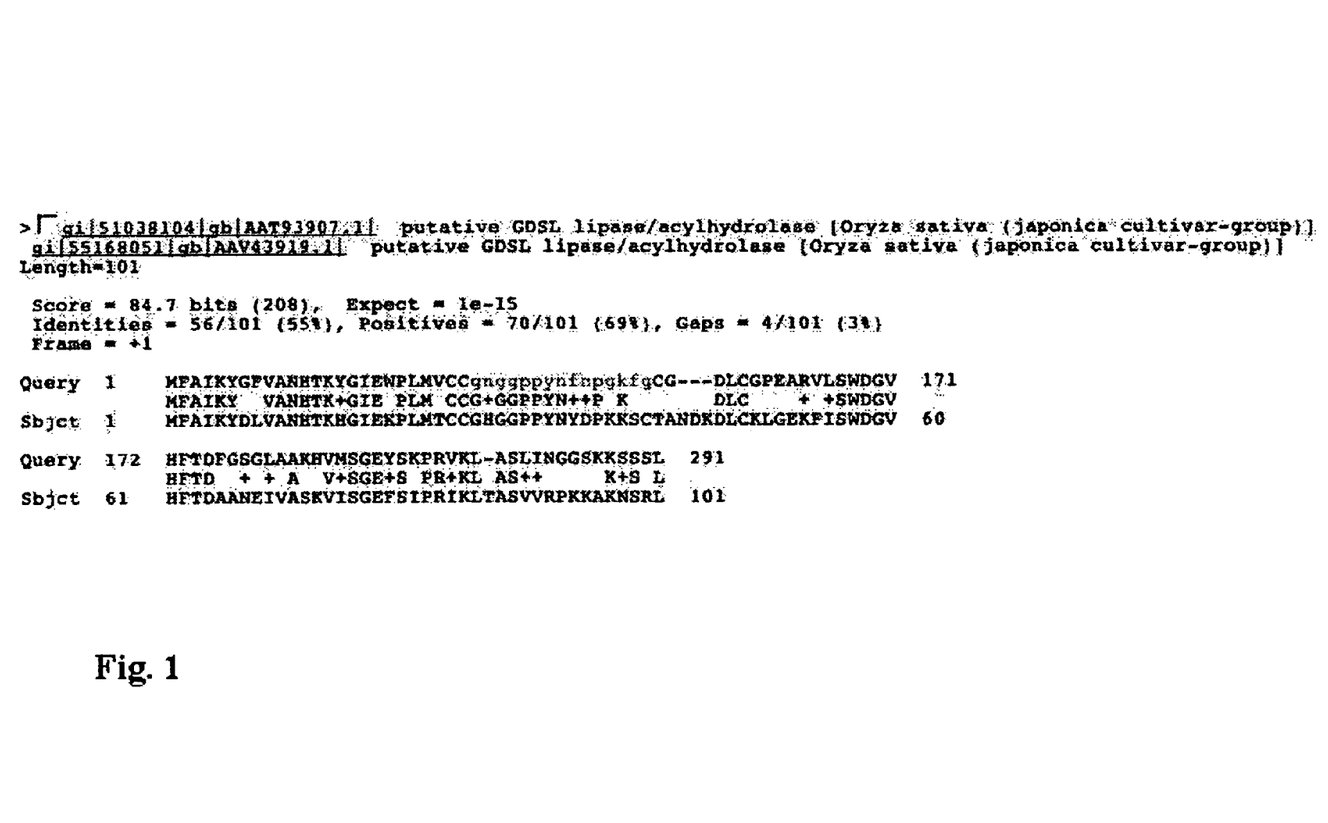
FIG. 1. shows the BLAST analysis of lipase clone 3F9 (SEQ ID NO:2) with a putative GDSL lipase/acylhydrolase of *Oryza sativa* (japonica cultivar-group) (SEQ ID NO:6).

This full length gene sequence was further compared with other gene sequences available in a public GeneBank (BLAST). The clone 3F9 showed homology (69% positive) with a putative GDSL lipase/acylhydrolase of *Oryza sativa* (japonica cultivar-group) having the sequence identified as AAT93907.1. The comparison is shown in FIG. 1.

Figure 2:
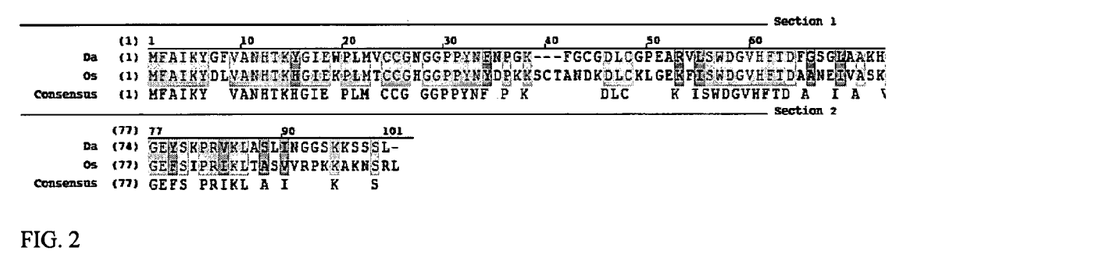
FIG. 2. illustrates a comparison of *Deschampsia antarctica* (Da) (SEQ ID NO:1) and *Oryza sativa* (Os) lipase protein-encoding gene (SEQ ID NO:6) showing the consensus region.

The alignment of lipase 3F9 clone with the putative GDSL lipase/acylhydrolase of *Oryza sativa* (japonica cultivar-group) gene was conducted by using the Vector NTI 7 software. The amino acid sequence for both lipases showed a 52.5% identity and 63.4% similarity (FIG. 2). This clearly indicates that the plant lipase gene of this disclosure is novel.

Figure 3:
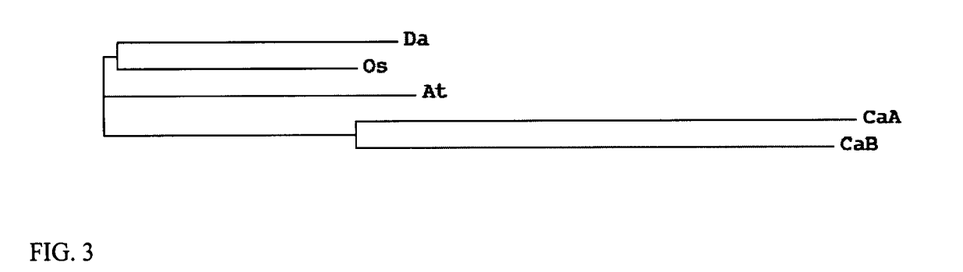
FIG. 3. depicts a phylogenetic tree displaying the inherited relationships between lipase 3F9 of *Deschampsia antarctica* (Da), putative GDSL lipase/acylhydrolase of *Oryza sativa* (Os), lipase homolog of *Arabidopsis thaliana* (At), lipase A (CaA) and lipase precursor B (CaB) of *Candida antarctica*.

A phylogenetic analysis of several plant and bacterial lipases was carried out in order to illustrate the presumed evolutionary relationships among them and to infer their evolutionary history. For this purpose, the lipase 3F9 of *Deschampsia antarctica* (Da), putative GDSL lipase/acylhydrolase of *Oryza sativa* (Os), lipase homolog of *Arabidopsis thaliana* (At), lipase A (CaA) and lipase precursor B (CaB) of *Candida antarctica* (FIG. 4) were compared. Finally, a phylogenetic tree was built (FIG. 3). It was found that there was no phylogenetic relationship between *Deschampsia antarctica* lipase 3F9 and lipase homolog of *Arabidopsis thaliana*, lipase B precursor and lipase A of *Candida antarctica*. The only phylogenetically related protein is the *Oryza sativa* lipase, which was previously demonstrated having only a 63.4% of similarity.

Figure 4:
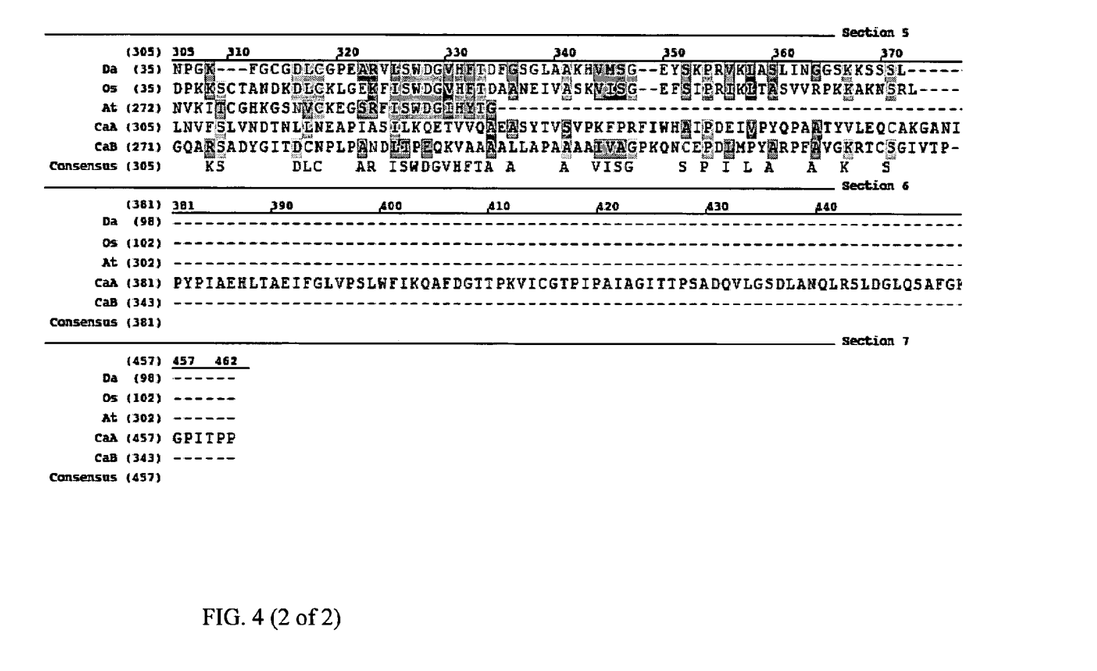
FIG. 4 shows an alignment of *Deschampsia antarctica* lipase (SEQ ID NO:2) with previously cloned lipases using the Vector NTI 7 software. *Deschampsia antarctica* lipase 3F9 (Da) (SEQ ID NO: 2), putative GDSL lipase/acylhydrolase of *Oryza sativa* (Os) (SEQ ID NO: 6), lipase homolog of *Arabidopsis thaliana* (At) (SEQ ID NO: 7), lipase A (CaA) (SEQ ID NO:8), and lipase precursor B (CaB) of *Candida antarctica* (SEQ ID NO:9) and consensus region.

In order to assure that *Deschampsia antarctica* 3F9 protein is novel a further comparison with functional related lipases was conducted by using a GenBank information. The simultaneous alignment of *D. antractica* lipase 3F9, putative GDSL lipase/acylhydrolase of *Oryza sativa*, lipase homolog of *Arabidopsis thaliana*, lipase B precursor and lipase A of *Candida antarctica* are shown in FIG. 4. The amino acid sequence of lipase 3F9 of *Deschampsia antarctica* showed 52.5% identity with lipase protein of *Oryza sativa*, 8.3% identity with lipase protein of *Arabidopsis thaliana*, only 2.4% identity with *Candida antarctica* chain A and 4.1% identity with *Candida antarctica* chain B.

The molecular weight of 3F9 lipase of *D. antarctica* is 10.3 kDa, while the molecular weight of lipase of *O. sativa* is 11.1 kDa, and that of *A. thaliana* is 33.3 kDa. The isoelectric point of 3F9 lipase of *D. antarctica* is 8.99, while that of lipase of *O. sativa* is 9.26 and the isoelectric point of lipase of *A. thaliana* is 9.20. Thus, clearly also the biochemical characterization of the instant plant lipase is distinct from the known proteins with similar function. The results from the sequence comparison and the biochemical analysis are summarized in Tables 1 and 2.

TABLE 1

Identity comparison of the amino acid sequence of lipase 3F9 of *D. antarctica* with other lipases.

| | *Deschampsia antarctica* (Da) | |
|---|---|---|
| | Similarity (%) | Identity (%) |
| *Oryza sativa* (Os) | 63.4 | 52.5 |
| *Arabidopsis thaliana* (At) | 11 | 8.3 |
| *Candida antarctica* chain A (CaA) | 5.4 | 2.4 |
| *Candida antarctica* chain B (CaB) | 8.2 | 4.1 |

TABLE 2

Biochemical comparison of lipase properties isolated from different sources.

| | Molecular Weight KDa | Isoelectric point |
|---|---|---|
| *Deschampsia antarctica* (Da) | 10.3 | 8.99 |
| *Orysa sativa* (Os) | 11.1 | 9.26 |
| *Arabidopsis thaliana* (At) | 33.3 | 9.20 |
| *Candida antarctica* chain A (CaA) | 49.2 | 5.33 |
| *Candida antarctica* chain B (CaB) | 33 | 5.80 |

The amino acid sequence of *Deschampsia antarctica* lipase deduced from DNA sequence is according to SEQ ID NO:2. The amino acid composition of the lipase protein encoded by DNA sequence is presented in Table 3.

TABLE 3

Amino acid composition of *Deschampsia antarctica* lipase deduced from DNA sequence.

| Amino Acid(s) | Number count | % by weight | % by frequency |
|---|---|---|---|
| Charged (RKHYCDE) | 27 | 33.36 | 27.84 |
| Acidic (DE) | 6 | 6.95 | 6.19 |
| Basic (KR) | 10 | 12.55 | 10.31 |
| Polar (NCQSTY) | 24 | 25.26 | 24.74 |
| Hydrophobic (AILFWV) | 30 | 32.66 | 30.93 |
| A Ala | 6 | 4.42 | 6.19 |
| C Cys | 4 | 4.01 | 4.12 |
| D Asp | 3 | 3.30 | 3.09 |
| E Glu | 3 | 3.65 | 3.09 |
| F Phe | 6 | 8.20 | 6.19 |
| G Gly | 15 | 9.31 | 15.46 |
| H His | 3 | 3.85 | 3.09 |
| I Ile | 3 | 3.25 | 3.09 |
| K Lys | 8 | 9.67 | 8.25 |
| L Leu | 7 | 7.59 | 7.22 |
| M Met | 3 | 3.70 | 3.09 |
| N Asn | 5 | 5.46 | 5.15 |
| P Pro | 6 | 5.71 | 6.19 |
| Q Gln | 0 | 0.00 | 0.00 |
| R Arg | 2 | 2.88 | 2.06 |
| S Ser | 9 | 7.82 | 9.28 |
| T Thr | 2 | 1.97 | 2.06 |
| V Val | 6 | 5.81 | 6.19 |
| W Trp | 2 | 3.38 | 2.06 |
| Y Tyr | 4 | 5.99 | 4.12 |
| B Asx | 8 | 8.77 | 8.25 |
| Z Glx | 3 | 3.65 | 3.09 |
| X Xxx | 0 | 0.00 | 0.00 |

The present invention is now further defined in the following examples. It should be understood that these examples, while indicating preferred embodiments of the invention, are given by way of illustration only. It would be apparent to one skilled in the art that various modifications of the invention in addition to those shown and described herein are within the scope of the invention.

EXAMPLE 1

Strains, Vectors and Culture Media

*Escherichia coli* strain DH5α (Invitrogen) was selected for vector construction and *Pichia pastoris* strain X-33 (Invitrogen) was used to express the *Deschampsia antarctica* lipase 3F9. *E. coli* was grown in low salt LB-Zeocin medium (1% tryptone, 0.5% yeast extract, 0.5% NaCl and 25 µg/ml of zeocin).

Pichia pastoris was grown in YPD medium (1% yeast extract, 2% peptone, 2% dextrose) for general growth and storage and in BMGY medium (1% yeast extract, 2% peptone, 100 mM potassium phosphate, pH 6.0, 1.34% YNB, $4\times10^{-5}$% biotin, 1% glycerol) or in BMMY medium (1% yeast extract, 2% peptone, 100 mM potassium phosphate, pH 6.0, 1.34% YNB, $4\times10^{-5}$% biotin, 0.5% methanol) to generate biomass or to induce expression, respectively. Zeocin 100 μg/ml agar plates were used (1% yeast extract, 2% peptone, 2% dextrose, 2% agar, 100 μg/ml zeocin) for selection of the transformants.

The *P. pastoris* X-33 and pPICZαB, used as fungal host and expression vector were purchased from Invitrogen Corporation.

EXAMPLE 2

Vector Construction and Transformation

Figure 5:
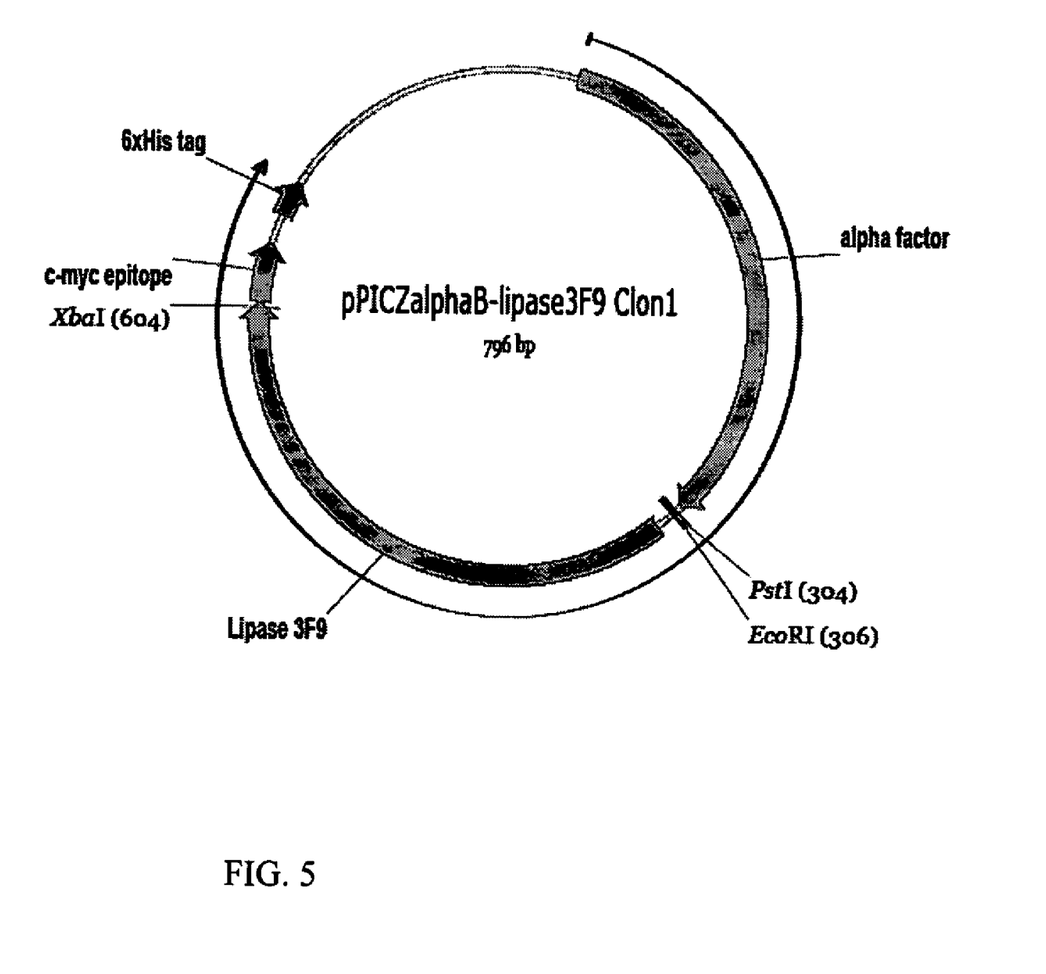
FIG. 5 depicts the expression vector pPICZalphaB-Lipase 3F9 Clon1 of *Deschampsia Antarctica*, the ORF with the alpha factor (secretor signal) and the 6×His tag to facilitate the protein purification.

The *Deschampsia antarctica* lipase 3F9 gene was isolated by polymerase chain reaction (PCR) amplification using de primers fw3F9 (5'CATGTTCGCCATCAAGTACG) SEQ ID NO:3 and rev3F9 (5' TCTAGAGATGATGATTTCTTG-GAGC) SEQ ID NO:4. This introduced a XbaI of the gene. PCR fragments were purified and DNA fragments were recovered from agarose gels using Ultra Clean 15 DNA purification Kit (Carlsbad, Calif., USA). DNA was purified and manipulated essentially as described by Sambrook et al., 1989. The PCR product was cloned into pGEM-T Easy (Promega) and liberated with the enzymes EcoRI and XbaI and ligated to the vector pPICZαB digested with the same restriction enzymes. This resulted in the expression vector pPICZalphaB-Lipase 3F9 Clon1 (FIG. 5). All amplifications by PCR were performed by using Taq DNA Polymerase recombinant LC (Fermentas, Hanover, USA).

The resulting plasmid constructs were transformed into *E. coli* and transformants were selected on low salt LB-Zeocin. The plasmid recombinant DNA was sequenced with 5-AOX1 promoter primer (5' GACTGGTTCCAATTGACAAGC) SEQ ID NO: 5 which annealed with the pPICZαB sequence. Sequence alignment was performed by BLAST.

EXAMPLE 3

Lipase Expression in *P. pastoris*

Electrocompetent cells of *P. pastoris* X-33 were prepared according to the supplier's instruction (Invitrogen). Ten micrograms recombinant plasmid linearized with PmeI was mixed with 80 μl electrocompetent cells, and electroporated by means of pulse discharge (1500 V, 25 F, Bio-Rad Gene Pulser) for 5 ms. After pulsing, 1 ml ice-cold 1M sorbitol was immediately added to the cuvette. Then, 200 μl aliquots were spread on YPDS plates (1% yeast extract, 2% peptone, 2% dextrose, 1M sorbitol, 2% agar, 100 μg/ml zeocin), and the plates were incubated at 30° C. to screen for zeocin resistant transformants according to their capacity to grow in the presence of zeocin. Resistant zeocin clones were grown on BMGY medium at 30° C. over night until $OD_{600}$=2-6 then transferred onto BMMY medium. Methanol was added to the culture medium to a final concentration of 0.5% (v/v) every 24 h to induce the lipase protein expression.

EXAMPLE 5

Induction of Lipase Production

Figure 6:
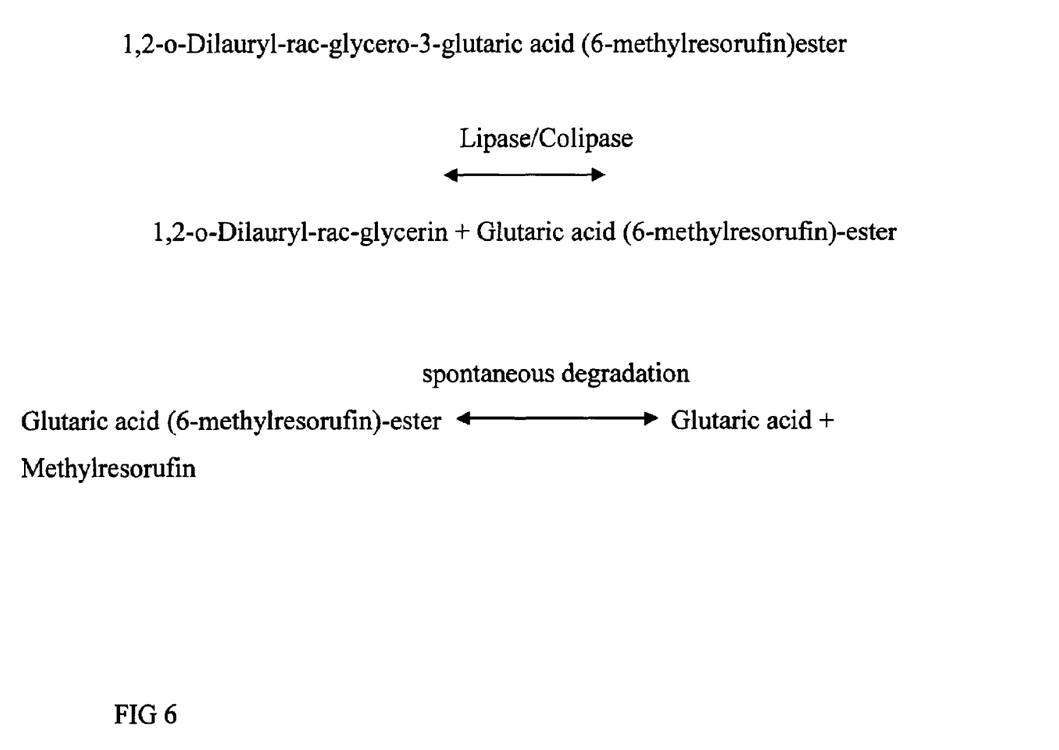
FIG. 6 shows the reaction sequence employed in the commercial kit to measure lipase activity in *P. pastori* cell culture.

Culture grown in BMGY for 96 hr was transferred into BMMY medium for induction of the inserted gen. Methanol was added to the culture medium to a final concentration of 0.5% (v/v) every 24 h for the following 3 days. The sample was collected by separating the culture medium by filtration and concentration of the culture broth. One aliquot of the sample was taken and lipase activity was measured using the commercial kit (Lipase DC FS (Diagnostic Systems International). The kit is based on the use of a synthetic substrate for lipase, which generates a colored product whose formation is evaluated in thermoregulated spectrophotometer at 580 nm (FIG. 6).

Figure 7:
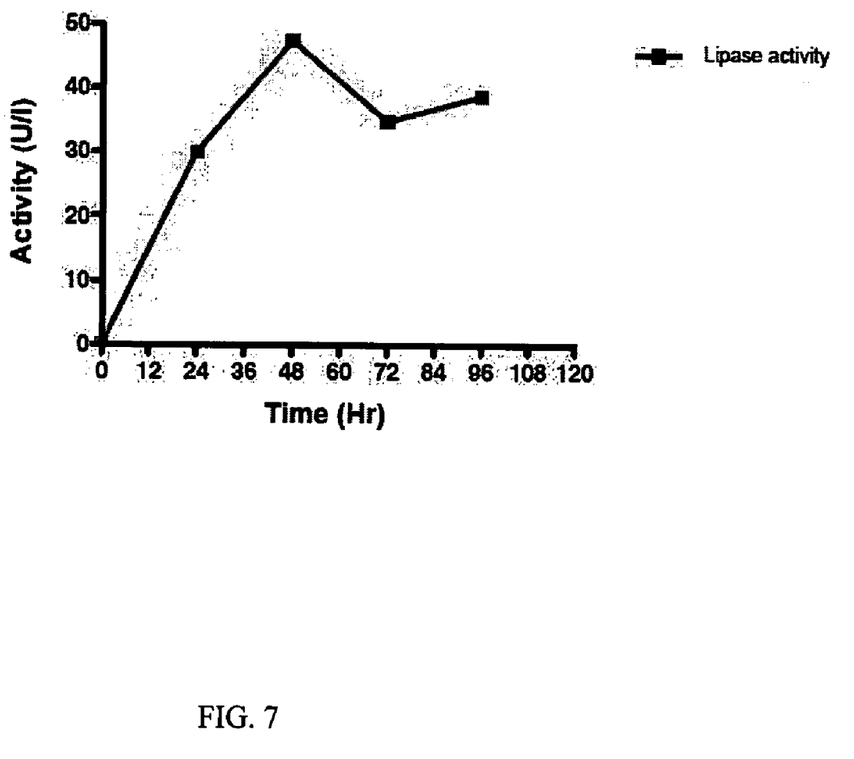
FIG. 7 illustrates the determination of lipase activity (U/L) at different induction times with methanol in *P. pastoris* broth.

FIG. 7 illustrates induction of the inserted gene in *P. pastori* (encoding the Da lipase enzyme production) by adding methanol to the broth culture. The maximum induction was reached at 48 h.

EXAMPLE 6

Lipase Activity at Different Temperatures

Figure 8:
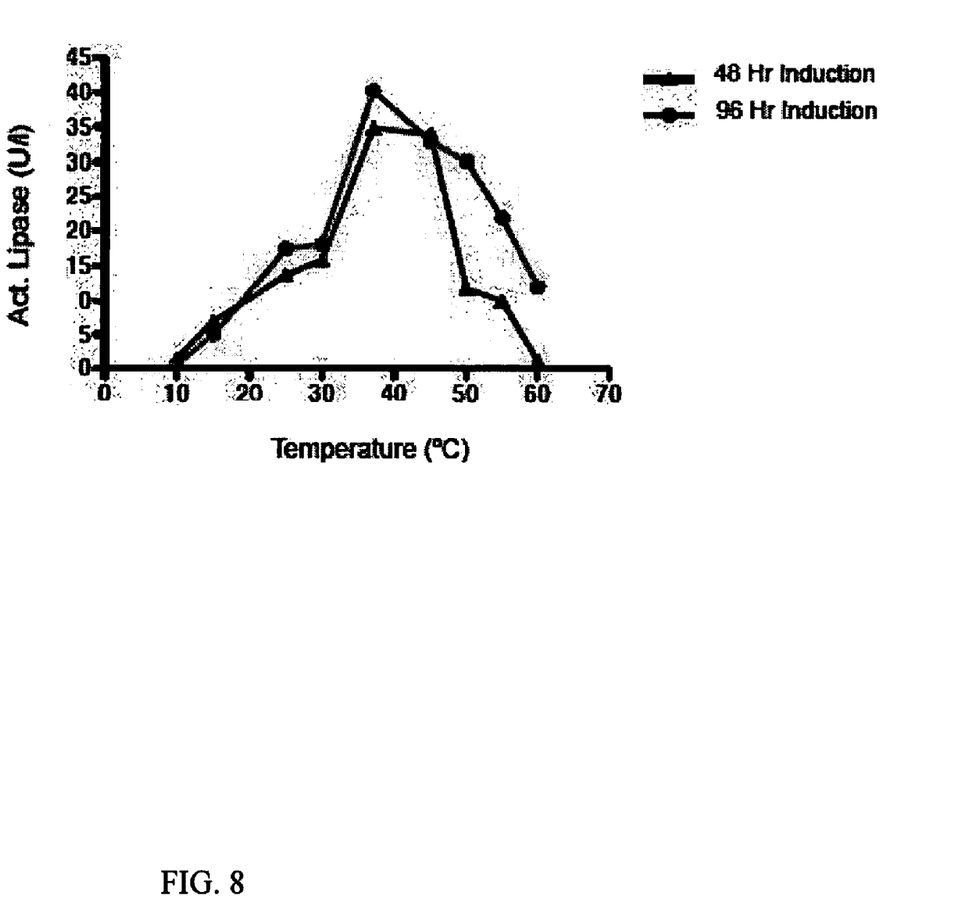
FIG. 8 illustrates lipase activity (U/L) at different temperature at 48 hours and 96 hours induction period.

Assay to determine the optimum temperature of *Deschampsia antarctica* cloned lipase was conducted next. Supernatant samples were removed from the induced media to measure the lipase activity. The activity was measured in a thermoregulated spectrophotometer at 580 nm in a temperature range from 10° C. to 60° C. The assays were run for two different induction times, 48 hours and 96 hours (FIG. 8). The maximum lipase activity was observed at 35-45° C. 50% of the activity was lost at 25° C. This behavior is characteristic of a psychrophilic enzyme.

EXAMPLE 7

Composition of a Sun Screen

Lipase enzymes are known to catalyze transesterification reaction resulting to feruly or coumaryl-substituted acylglycerols. Such acylglycerols are known to be efficient as sun screen agents.

The lipase enzyme according to the present invention is psychrophilic, i.e. it has low optimal temperature and at ambient temperatures it clearly has a high activity. Based on this characteristic a preferred embodiment of the instant invention is to use the novel lipase enzyme as a compound in sun screen lotion. Other components of the lotion would comprise triglycerides from natural origin, antioxidant compound that could act as photoreceptors and having at least one carboxyl group on its structure and other compound necessary for a spray formulation. Examples of triglycerides are glycerine, coconut oil, olive oil, rapeseed oil among others. The photoreceptor agent could be for example cinnamic acid, ferulic acid, quinic acid, shikimic acid, or the other antioxidants from *Deschampisa antarctica*. Any of the isolated optical stereoisomer, or derivatives as well as their mixtures, can be used in the composition of the invention. As the psychrophilic lipase is able to react under very mild conditions (FIG. 8)) it will initiate the esterification reaction between natural oils and photoreceptor once the lotion in sprayed on the skin and the sunlight UV-B rays reaches it.

EXAMPLE 8

Use of the Lipase Enzyme in Waste Water Cleaning

The lipase enzyme according to this disclosure can be used in a method for the continuous treatment to clean wastewater coming from different sources, mainly containing oil, fats waxes or any esterified compounds present during mil processing, soap producing, tannin industry and other related industries in a treatment plant. Such method comprises the steps of: a) providing a mixture comprising active amounts of an enzyme comprising a psycrophilic lipase (immobilized or not); b) immersing said mixture in fresh water for about 1 hour to about 3 hours at water temperature (ranging from 4 to 20° C.) in order to provide an activated mixture; c) mixing a volume of aqueous water waste from said treatment plant with a volume of said enzyme from about 2 hours to about 48 hours at room temperature to produce an acclimated mixture; d) adding a volume of said acclimated mixture to a wastewater treatment tank in said treatment plant and; e) maintaining said mixture and said wastewater in contact at water temperature for one to three days to reduce the amount of undesirable oil, fats and wastes and suspended solids in the treatment plant.

What is claimed is:

1. An isolated nucleic acid molecule encoding plant lipase comprising the amino acid sequence of SEQ ID NO: 2.

2. The isolated nucleic acid molecule of claim 1, wherein the nucleic acid comprises SEQ ID NO:1.

3. An isolated nucleic acid sequence consisting of SEQ ID NO:1 and encoding a plant lipase having the amino acid sequence of SEQ ID NO:2.

4. An expression vector comprising the nucleic acid of claim 1.

5. The expression vector of claim 4, wherein the vector further comprises a secretor signal and 6×His tag.

6. The vector of claim 5, wherein the secretor signal is alpha factor.

7. A host cell comprising the expression vector of claim 4.

8. The cell according to claim 7, wherein the cell is a *Pichia* cell.

9. A process for producing recombinant lipase encoded by SEQ ID NO:1 by cultivating *Pichia* cells of claim 8 and recovering the lipase from the culture medium.

* * * * *

UNITED STATES PATENT AND TRADEMARK OFFICE
CERTIFICATE OF CORRECTION

PATENT NO. : 7,485,445 B2  Page 1 of 1
APPLICATION NO. : 11/787383
DATED : February 3, 2009
INVENTOR(S) : Manuel Gidekel It is certified that error appears in the above-identified patent and that said Letters Patent is hereby corrected as shown below:

Title Page:

Section [75], Please delete; "Gustavo Gabrera"

Please insert; --Gustavo Cabrera--

Signed and Sealed this

Tenth Day of November, 2009

David J. Kappos
*Director of the United States Patent and Trademark Office*

```
                            SEQUENCE LISTING

<160> NUMBER OF SEQ ID NOS: 5

<210> SEQ ID NO 1
<211> LENGTH: 291
<212> TYPE: DNA
<213> ORGANISM: Deschampsia antarctica

<400> SEQUENCE: 1
atgttcgcca tcaagtacgg cttcgttgcc aaccacacca aatatgggat tgagtggcca      60
ttaatggtgt gctgcgggaa cggcggcccg ccttacaact tcaacccagg aaagtttgga     120
tgcggcgatc tctgcgggcc ggaggcgagg gtgctgagct gggacggtgt gcacttcacc     180
gatttcggca gcggccttgc cgccaagcat gttatgagtg gtgagtactc caagcctaga     240
gtaaagctgg caagcctgat caatggtggc tccaagaaat catcatctct a              291

<210> SEQ ID NO 2
<211> LENGTH: 97
<212> TYPE: PRT
<213> ORGANISM: Deschampsia antarctica

<400> SEQUENCE: 2

Met Phe Ala Ile Lys Tyr Gly Phe Val Ala Asn His Thr Lys Tyr Gly
1               5                   10                  15

Ile Glu Trp Pro Leu Met Val Cys Cys Gly Asn Gly Gly Pro Pro Tyr
            20                  25                  30

Asn Phe Asn Pro Gly Lys Phe Gly Cys Gly Asp Leu Cys Gly Pro Glu
        35                  40                  45

Ala Arg Val Leu Ser Trp Asp Gly Val His Phe Thr Asp Phe Gly Ser
    50                  55                  60

Gly Leu Ala Ala Lys His Val Met Ser Gly Glu Tyr Ser Lys Pro Arg
65                  70                  75                  80

Val Lys Leu Ala Ser Leu Ile Asn Gly Gly Ser Lys Lys Ser Ser Ser
                85                  90                  95

Leu

<210> SEQ ID NO 3
<211> LENGTH: 20
<212> TYPE: DNA
<213> ORGANISM: artificial sequence
<220> FEATURE:
<223> OTHER INFORMATION: Primer fw3F9

<400> SEQUENCE: 3
catgttcgcc atcaagtacg                                                   20
```

```
<210> SEQ ID NO 4
<211> LENGTH: 25
<212> TYPE: DNA
<213> ORGANISM: artificial sequence
<220> FEATURE:
<223> OTHER INFORMATION: primer rev3F9

<400> SEQUENCE: 4
tctagagatg atgatttctt ggagc                                              25

<210> SEQ ID NO 5
<211> LENGTH: 21
<212> TYPE: DNA
<213> ORGANISM: artificial sequence
<220> FEATURE:
<223> OTHER INFORMATION: 5-AOX1 promoter primer

<400> SEQUENCE: 5
gactggttcc aattgacaag c                                                  21
```